United States Patent

Busnel et al.

[11] Patent Number: 5,804,628
[45] Date of Patent: Sep. 8, 1998

[54] ELASTOMER FILM, PROCESS FOR ITS PREPARATION AND ITS APPLICATIONS

[75] Inventors: René Guy Busnel, Bievres; André Cheymol, Dange Saint Romain; Gérard Riess, Mulhouse, all of France

[73] Assignee: Hutchinson, Paris, France

[21] Appl. No.: 505,313

[22] PCT Filed: Dec. 22, 1994

[86] PCT No.: PCT/FR94/01515

§ 371 Date: Nov. 6, 1995

§ 102(e) Date: Nov. 6, 1995

[87] PCT Pub. No.: WO95/17453

PCT Pub. Date: Jun. 29, 1995

(Under 37 CFR 1.47)

[30] Foreign Application Priority Data

Dec. 23, 1993 [FR] France ................... 93 15561

[51] Int. Cl.⁶ ............... C08K 5/19; C08L 83/04; A01N 25/04
[52] U.S. Cl. ............... 524/377; 524/376; 524/504; 524/505; 427/2.3; 604/292; 128/844; 424/405
[58] Field of Search .................. 524/377, 376, 524/504, 505; 427/2.3; 604/292; 128/844; 424/405

[56] References Cited

U.S. PATENT DOCUMENTS

| 2,947,282 | 8/1960 | Brown ................... 119/14.47 |
| 4,725,575 | 2/1988 | Frihart et al. ................... 512/4 |
| 4,930,522 | 6/1990 | Busnel et al. ................... 128/844 |
| 5,024,852 | 6/1991 | Busnel et al. ................... 427/2.3 |
| 5,104,649 | 4/1992 | Jansson et al. ................... 424/78.31 |

FOREIGN PATENT DOCUMENTS

| 459228 | 3/1975 | Australia . |
| 141628 | 5/1985 | European Pat. Off. . |
| 338821 | 10/1989 | European Pat. Off. . |
| 2600656 | 12/1987 | France . |
| 1494024 | 6/1969 | Germany . |
| 3035851 | 4/1981 | Germany . |
| 7308061 | 12/1973 | Netherlands . |
| 372776 | 6/1932 | United Kingdom . |
| 1179497 | 1/1970 | United Kingdom . |
| 2263114 | 7/1993 | United Kingdom . |

OTHER PUBLICATIONS

JP,A,57 185 326, Nov. 15, 1982, Abstract, Database WPI, Week 8326, Derwent Publications Ltd., London, GB, AN 83–61887K.

Primary Examiner—Vasu Jagannathan
Assistant Examiner—John J. Guarriello
Attorney, Agent, or Firm—Bell Seltzer Intellectual Property Law Group of Alston & Bird LLP

[57] ABSTRACT

Elastomer films in which active chemical substances such as anticorrosive agents, lubricants or medications such as biocides are uniformly dispersed in the form of liquid droplets, process for their preparation and their applications.

Stable emulsions comprising a continuous phase made up of a solution of elastomer in an organic solvent and a disperse phase including at least one active chemical substance in a solvent which is not miscible with the solution of elastomer, which are capable of being converted into elastomer films, and process for their preparation.

The said elastomer film includes a dispersion of droplets of a solvent b which is not miscible with the elastomer, laden with at least one active chemical substance, which dispersion is stabilized by a block or graft copolymer comprising polyB blocks which are miscible with the said droplets and polyA blocks which are not miscible with these droplets.

27 Claims, 5 Drawing Sheets

ELASTOMER FILM, PROCESS FOR ITS PREPARATION AND ITS APPLICATIONS

The present invention relates to elastomer films in which there are uniformly dispersed, in the form of liquid droplets, active chemical substances such as anticorrosive agents, lubricants or else biocides for medical use; it also covers the processes of preparation and the various applications of these films.

The present invention also relates to stable emulsions comprising a continuous phase made up of a solution of elastomer in an organic solvent and a disperse phase including an active chemical substance in a solvent that is not miscible with the solution of elastomer, which are capable of being converted into elastomer films, and to the process for their preparation.

The various elastomer materials usually employed in the medical or paramedical field (especially hygiene) can be modified, so as to be used in combination with active chemical substances which have a protective action, when these materials are employed (gloves, fingerstalls, protective sheaths, tapes and various dressings).

In fact, both in the cases of examination or surgical intervention or in odontology, and for the protection against pathogenic agents such as, for example, bacteria, viruses and fungal spores, a rupture or even sometimes merely the pores or a crack in the elastomer membrane can give rise to a contamination of the carrier of the said material, the use of which is thus not free from risk, especially since in the practice of these occupations, pricks with syringes, suture needles, a trocar, bone fragments and the like take place relatively frequently.

Various treatments have been proposed in order to try to reduce the risk margin in the use of products manufactured with these elastomer materials:

the dispersion of an active substance in liquid form in the elastomer, as a plasticizer for the latter; however, in this case the liquid is not very available as such, since it is bonded to the elastomer. Moreover, in the case where part of this chemical substance is not bonded to the elastomer, the liquid containing the said chemical substance, which is not bonded, can give rise to a macroscopic phase separation and to migration phenomena in the course of time; moreover, the liquid concentrates in some regions, thus leaving a whole surface of the elastomer without active substance;

the liquid may be incorporated between two sheaths of elastomer which are not integrally joined; in this case it no longer acts as a plasticizer and exhibits a greater availability. However, such a treatment has the disadvantage of placing the active substance in direct contact with the elastomer, which affects the latter by destroying its mechanical properties and therefore, consequently, its imperviousness. Moreover, the liquid present between the two sheaths tends, when friction takes place, to collect in a single place, also leaving a whole surface of the material without active substance (U.S. Pat. No. 2,586,674);

to overcome these disadvantages, the Applicant Company has introduced a microencapsulated liquid into an elastomer material, either between two layers of elastomer material (Application EP 306 389) or into the elastomer material (International Application WO 93/02668). The use of microcapsules makes the liquid effectively available as such; however, the walls of the microcapsules may be found difficult to pierce and in some cases they modify the mechanical properties of the elastomer.

Consequently, in continuing its research, the Applicant Company set itself the objective of developing an elastomer material which does not exhibit the disadvantages of the materials filled with active chemical substance of the prior art, especially:

in that the liquid containing the active chemical substance is available both in the case of tearing and merely by means of rubbing, in the form of stabilized fine droplets, uniformly in the whole of the said material, the liquid not being concentrated in some regions of the latter, and in that the mechanical properties of the said material are not modified.

The subject of the present invention is an elastomer film including an active chemical substance in liquid form, which film is characterized in that it includes a dispersion of droplets of a solvent b which is not miscible with the elastomer, laden with at least one active chemical substance (solution or dispersion), which dispersion is stabilized by a block or graft copolymer comprising at least polyB blocks which are miscible with the said droplets and polyA blocks which are not miscible with these droplets.

According to an advantageous embodiment of the said elastomer film, the said solvent b is selected from polyols, preferably from polypropylene glycol, polyethylene glycol and glycerol.

According to another advantageous embodiment of the said elastomer film, the stabilizing (block or graft) copolymer is selected from diblock copolymers of polyA-block-polyB type, triblock copolymers of polyB-block-polyA-block-polyB (BAB) type, of polyA-block-polyB-block-polyA (ABA) type, of polyA-block-polyB-block-polyC (ABC) or polyA-block-polyC-block-polyB (ACB) type and graft copolymers of polyA-graft-polyB or polyB-graft-polyA type, of polyA-graft-polyB and polyC type or of polyC-graft-polyA and polyB type.

According to another advantageous embodiment of the said elastomer film, the proportions of polyA blocks are between 10 and 90% and the proportions of polyB blocks are between 90 and 10% (relative to the sum of the polyA blocks+polyB blocks) and the proportions of polyC blocks are between 0% and 50% (relative to the total of blocks).

According to yet another advantageous embodiment of the said elastomer film, the molecular masses of the polyA and polyB blocks are between 1000 and 500000 daltons.

In accordance with the invention, the polyA blocks are chosen from the group which includes polydienes, polyolefins, polyethers or silicones, such as polyisoprene, polybutadiene, polyisobutene, hydrogenated polybutadiene or hydrogenated polyisoprene, polystyrene, poly-tert-butylstyrene, polyoxypropylene or polydimethyl-siloxane, which are miscible with a solution of elastomer in an apolar or weakly polar solvent a and not miscible with the solvent b, and the polyB blocks, which are miscible with the solvent b, are chosen from the group which includes polyoxyethylene, polyvinylpyrrolidone, polyacrylic acids, poly(vinyl alcohol) and quaternized poly(vinylpyridine).

Among the graft structures containing polyA, polyB and polyC blocks there may be mentioned especially the Goldschmidt LE 2229® copolymer, which corresponds to a graft structure where:

the polyC blocks are, for example, acrylic chains, the polyA blocks are alkyl chains, and the polyB blocks are poly(oxyethylene) blocks.

In such copolymers the polyA blocks are blocks that are miscible with the elastomer solution (apolar solvent a), the polyB blocks are miscible with the solvent b and the polyC blocks may be either miscible with the solvent a or the solvent b, or not miscible with the solvents a and b.

The elastomer may be selected, this being without any limitation being implied, from polybutadiene, polyisoprene, polychloroprene, SBR (styrene butadiene rubber), NBR (nitrile butadiene rubber), SBS (styrene butadiene styrene), SIS (styrene isoprene styrene) or SEBS copolymers, of molecular mass which is preferably higher than 50 000.

Such an elastomer film, in which the liquid containing the active chemical substance(s) is dispersed, uniformly and stably, in the form of fine droplets makes the said active substance(s) which is (are) included in the elastomer material immediately available and effective, even in the case of rubbing (absence of intermediate layer or of microcapsule walls). The liquid droplets, with a diameter of between 0.1 to 100 µm, are actually sufficiently large to provide liquid in a sufficient quantity at the appropriate time.

In an alternative form the block copolymer acts both as an agent for stabilizing the emulsion and as active substance.

Such a block copolymer is advantageously preferably PMDS-POE (biocidal activity), namely a polydimethylsiloxane-polyoxyethylene block copolymer.

The elastomer film according to the invention, which may advantageously be used as coating for supports made especially of elastomer or for overmoulding a rubbing seal, exhibits, in particular, the following advantages:

in the medical and paramedical field: the gloves, fingerstalls, protective sheaths or dressings coated with an elastomer film in accordance with the invention offer a gain in reliability and safety;

in industry: coatings of an elastomer film in accordance with the invention can advantageously be employed in any industries where it is desirable that a chemical substance should be released by rubbing, especially in the motor vehicle industry, where such coatings may form an overmoulding of a rubbing seal.

Another subject of the present invention is a process for the preparation of the said elastomer film, characterized in that it includes:

(a) the preparation of an emulsion which includes:
the preparation of a phase A by dissolving the elastomer in an organic solvent a (phase A: solution of elastomer in the organic solvent a);
the preparation of a phase B, by mixing at least one active substance into an organic solvent b which is not miscible with the phase A (phase B: solution or dispersion of active substance in an organic solvent b which is not miscible with the phase A);
the addition to the phase A or to the phase B, in proportions of 0.1 to 50%, preferably of 0.1 to 25%, of a block or graft copolymer containing at least polyA blocks which are miscible with the phase A (solution of elastomer in an organic solvent a) and polyB blocks which are miscible with the phase B, as defined above;
the dispersion of the phase B in the phase A in order to obtain an emulsion in which the phase A forms the continuous phase and the phase B the disperse phase; and (b) the evaporation of the organic solvent a, in order to obtain an elastomer film containing, in the form of a stable dispersion, droplets of solvent b laden with active chemical substance.

The polyA blocks must be miscible with the phase A (solution of elastomer in the solvent a) and not miscible with the phase B, whereas they may be either miscible or not with the elastomer; the polyB blocks are miscible only and selectively with the phase B.

This rule of selective miscibility is necessary for obtaining the stability and for the ability to adjust the particle size of disperse phase (phase B) of the starting emulsion made up of a hydrophilic phase (or polar phase) and of a hydrophobic phase (or apolar phase), which is used for preparing the film by evaporation of the organic solvent a.

The elastomer solution is advantageously produced by dissolving an elastomer, as defined above (polybutadiene, polyisoprene, polychloroprene, SBR, NBR, SBS, SEBS or SIS copolymers), in an apolar or weakly polar organic solvent a chosen especially from aromatic, aliphatic and alicyclic hydrocarbons, for example paraffinic hydrocarbons, cyclohexane, benzene, toluene, xylene, tetralin, decalin or a mixture thereof.

Equally advantageously, the phase B is produced by mixing an active substance into a solvent b selected from polyols, preferably from polypropylene glycol, polyethylene glycol and glycerol or mixtures thereof.

When the active chemical substance is chosen from molecular complexes of the class of the antiseptics, it preferably forms part of the group consisting of quaternary ammoniums, in particular dimethyldidecyl-ammonium, block copolymers with biocidal activity, such as the polydimethylsiloxane-polyoxyethylene block copolymer, biguanides (water-soluble salts of chlorhexidine, such as, for example, chlorhexidine digluconate), phthalaldehyde, phenolic derivatives (hexachlorophene), nonionic surfactants containing a polyoxyethylene block, such as octoxynol (Triton® X100) and hexamidine, which are employed on their own or as a mixture, especially a dimethyldidecylammonium-PMDS-POE block copolymer mixture, or one of the mixtures of antiseptics as described in Patent Application EP 0 555 116 (quaternary ammonium—water-soluble chlorhexidine salt, nonionic antiseptic—hexamidine, quaternary ammonium—nonionic antiseptic, and nonionic antiseptic—water-soluble chlorhexidine salt).

According to another advantageous embodiment of the said process, the said stabilizing copolymer (block or graft) is selected from diblock copolymers, of polyA-block-polyB type, triblock copolymers of polyB-block-polyA-block-polyB (BAB) type, of polyA-block-polyB-block-polyA (ABA) type, of polyA-block-polyB-block-polyC (ABC) or polyA-block-polyC-block-polyB (ACB) type and graft copolymers of polyA-graft-polyB or polyB-graft-polyA type, of polyA-graft-polyB and polyC type or of polyC-graft-polyA and polyB type.

According to another advantageous embodiment of the said process, the proportions of polyA blocks are between 10 and 90% and the proportions of polyB blocks are between 90 and 10% (relative to the sum of polyA blocks+polyB blocks) and the proportions of polyC blocks are between 0% and 50% (relative to the total of blocks).

According to another advantageous embodiment of the said process the molecular masses of the polyA and polyB blocks are between 1000 and 500000 daltons.

The polyA and polyB blocks are such as defined above.

Another subject of the present invention is an emulsion capable of being employed for the preparation of an elastomer film, characterized in that it includes:

a phase A including an elastomer dissolved in an organic solvent a (hydrophobic or apolar phase), in which is dispersed a phase B including at least one active chemical substance in solution or dispersed in a solvent b (hydrophilic or polar phase) which is not miscible with the phase A, and a block or graft copolymer comprising at least polyA blocks which are miscible with the phase A and polyB blocks which are miscible with the phase B.

Such emulsions of hydrophilic phase—hydrophobic phase type, containing such a block or graft copolymer which acts as a stabilizer of the emulsion, are particularly stable.

The solvents a, b, the block or graft copolymer and the elastomer are as defined above.

Another subject of the present invention is a process for the preparation of the said stable emulsions, characterized in that it includes:

the preparation of a phase A by dissolving the elastomer in an organic solvent a;

the preparation of a phase B by mixing at least one active substance into an organic solvent b which is not miscible with the phase A;

the addition to the phase A or to the phase B, in proportions of 0.1 to 50%, preferably of 0.1 to 25%, of a block or graft copolymer comprising at least polyA blocks which are miscible with the phase A and polyB blocks which are miscible with the phase B;

the dispersion of the phase B in the phase A in order to obtain an emulsion in which the phase A forms the continuous phase and the phase B the disperse phase.

Another subject of the present invention is the various applications of the elastomer film according to the invention as coating for supports (elastomers, plastics etc.).

BRIEF DESCRIPTION OF THE DRAWINGS

Besides the arrangements which precede, the invention further includes other arrangements which will emerge from the description that is to follow, which refers to examples of embodiment of the process forming the subject of the present invention, with reference to the attached drawings, in which.

It must be clearly understood, however, that these examples are given merely by way of illustration of the subject of the invention and that they do not constitute any limitation whatever thereof.

EXAMPLE 1 a) Preparation of a stable emulsion in accordance with the invention:

Preparation of the continuous phase (phase A):

Synthetic polyisoprene (PI) of molecular mass of between 1000000 and 2000000 is dissolved with stirring in cyclohexane, so as to obtain a solution containing 7.5% of polyisoprene.

Preparation of the disperse phase (phase B):

Bardac® (dimethyldidecylammonium chloride) is dissolved with stirring in glycerol so as to obtain a solution containing 10.8% of Bardac®.

Addition of stabilizing copolymer:

A POE-PI-POE triblock copolymer (of BAB type), that is to say poly(oxyethylene)-block-polyisoprene-block-poly(oxyethylene) was synthesized by anionic polymerization. Its weight content of PI (determined by $^1$H NMR) is 50.1%; the number-average molecular mass of the PI is 78000 (determined by GPC) and its total molecular mass is 156000.

This copolymer, dissolved in cyclohexane, is added to the polyisoprene solution (phase A) in a proportion of 2% on a mass basis relative to the polyisoprene.

Preparation of the emulsion:

22.3% of phase B (glycerol+Bardac®), relative to the PI, are added to the phase A with stirring at ambient temperature.

A stable emulsion is thus obtained in which the size of the disperse phase is, on average, 3 µm.

Figure 1A:
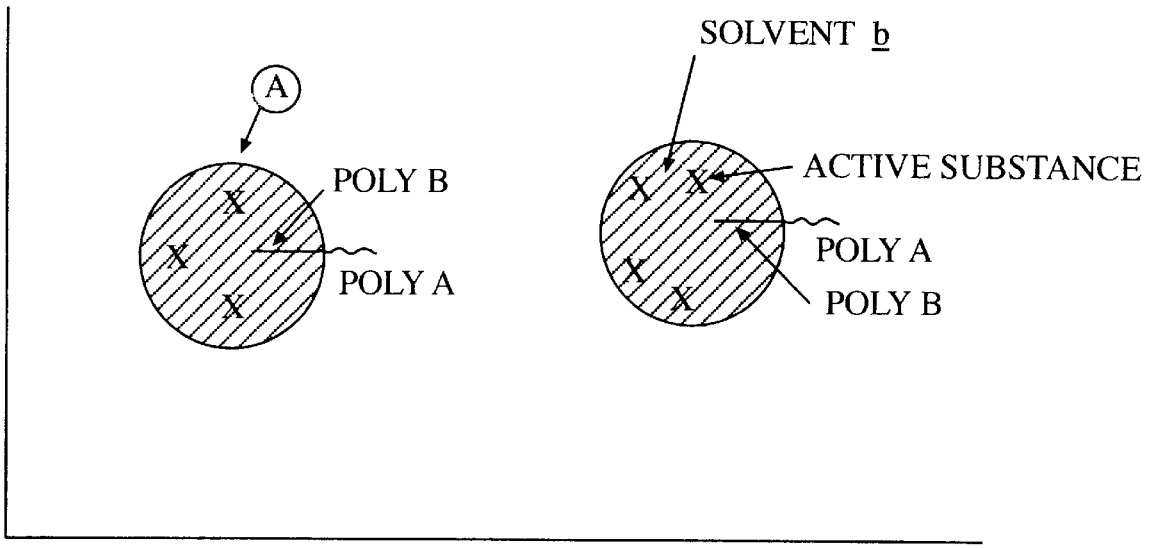
FIGS. 1a,b show the structure of the emulsion and of the film in accordance with the invention.
Figure 1B:
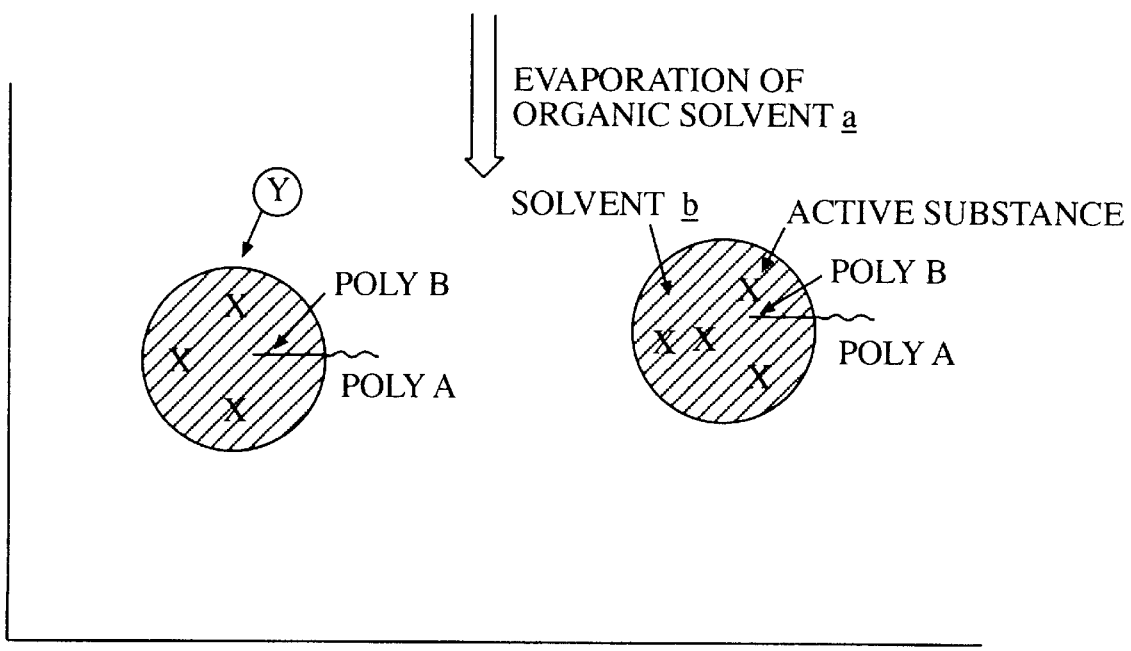

The structure is illustrated in FIG. 1a, in which Ⓐ denotes the continuous phase A (elastomer in solution in the organic solvent a), /// denotes the disperse phase B (glycerol), xxx denotes the biocide dissolved in the said phase B and ~~~~ denotes the block copolymer acting as a stabilizer for the emulsion.

b) Preparation of an elastomer film:

The cyclohexane present in the emulsion obtained in a) is evaporated at ambient temperature and at atmospheric pressure. The structure is illustrated in FIG. 1b, in which the phase B and the biocide are shown in the same way as in FIG. 1a and Ⓨ denotes the elastomer film.

An elastomer is obtained containing droplets which are, on average, 3 µm in size. These droplets enclosing the active substance represent 22.3% of the mass of the total material. They are dispersed uniformly in the elastomer, which retains excellent elastic properties.

EXAMPLE 2

The operation is carried out as in Example 1, also employing the same components.

However, the proportion of phase B is increased by being raised from 22.3 to 42.2% relative to the PI.

The content of POE-PI-POE copolymer is raised from 2 to 4.15% relative to the PI.

In these conditions a stable emulsion is obtained in which the size of the disperse phase is, on average, 4 µm. The elastomer obtained after evaporation of the solvent encloses droplets of glycerol+Bardac® which are of the order of 4 µm in size.

EXAMPLE 3

The procedure is as in Example 2, the POE-PI-POE copolymer being replaced with a PI-POE diblock copolymer, the characteristics of which are as follows:

number-average molecular mass of the PI block: 44 000, mass percentage of PI in the copolymer: 47%, total molecular mass: 94 000.

This copolymer, dissolved in a cyclohexane-tetrahydrofuran mixture (2:1 by volume), is added to the polyisoprene solution in a proportion of 4.3% by mass relative to the polyisoprene.

With a proportion of phase B of 42.5% relative to the PI a stable emulsion is obtained in which the size of the disperse phase is, on average, 8 µm.

The elastomer film obtained after evaporation of the solvent encloses droplets of glycerol+Bardac® which are of the order of 8 µm in size.

EXAMPLE 4 a) The procedure is as in Example 2, the POE-PI-POE copolymer being replaced with a polydimethylsiloxanepoly(oxyethylene) graft copolymer which has a mass content of POE of 77.3% and of PDMS of 22.7%. This copolymer is marketed by the Goldschmidt company (Germany) under the name Tegopren 5843®. It is introduced in a proportion of 5.6% relative to the PI.

As above, a stable emulsion is obtained which, after evaporation of the cyclohexane, produces a material enclosing droplets of glycerol+Bardacs® which are of the order of 6 μm in size.

Because of the presence of a constituent of silicone type, this material additionally exhibits advantageous surface-lubricating properties.

This copolymer acts as a stabilizing agent for the emulsion. In addition, because of its high POE content, it is a lubricant which is partially soluble in the solvent b (glycerol+Bardac®).

b) A whole series of films in accordance with the invention can be obtained by proceeding as in a) but by varying the concentration of Tegopren 5843® from 5.6 to 40% relative to the PI.

EXAMPLE 5

In the examples below the procedure is as in Example 1, the concentrations of bioactive substances and of solvent b being varied while conforming to FIGS. 2 to 5 (ternary diagrams), that is say by choosing concentrations corresponding to the immiscible region of the said ternary diagrams.

Figure 2:
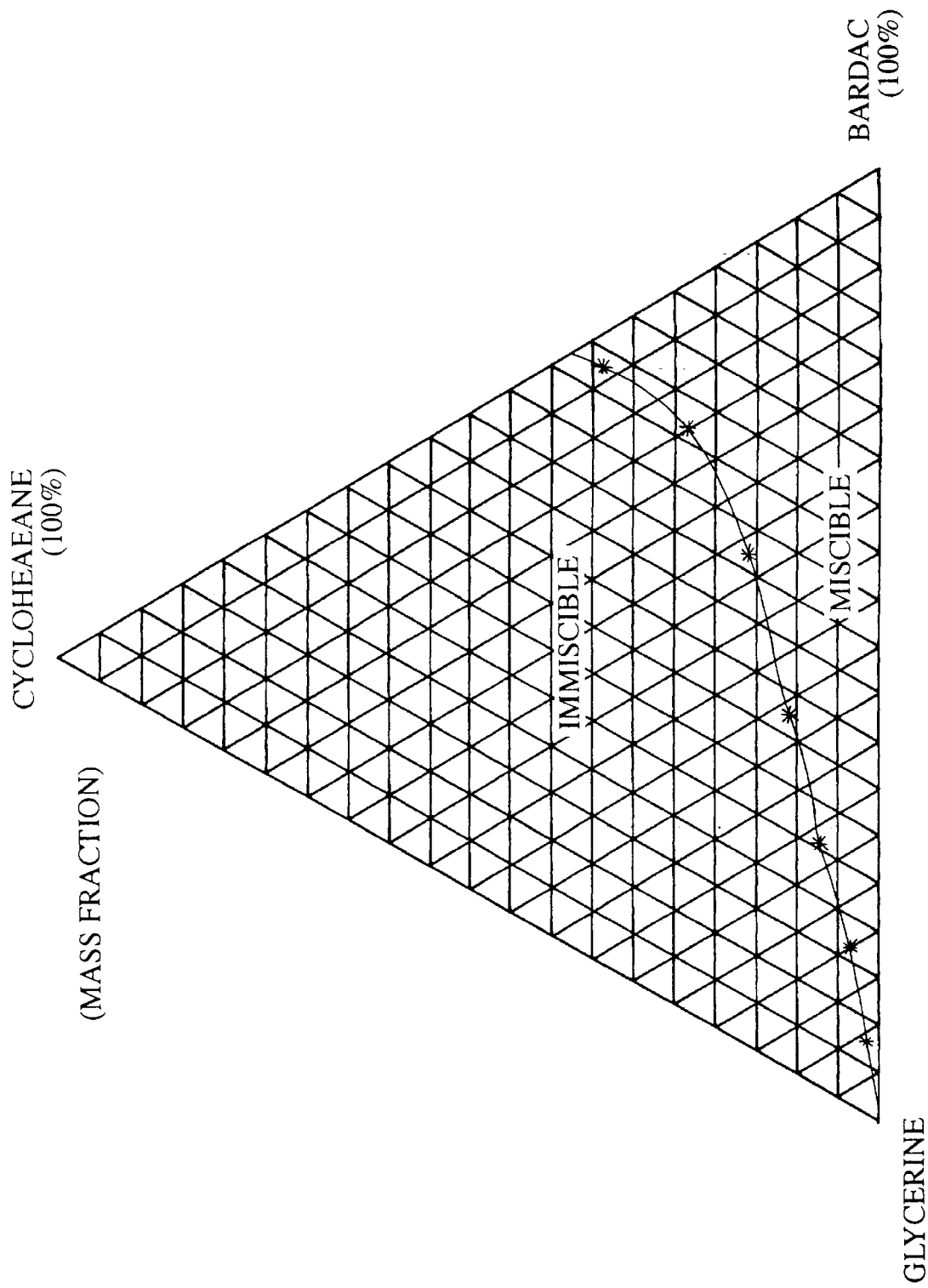
FIGS. 2 to 5 illustrate ternary diagrams of solvent a/solvent b/bioactive substance.

FIG. 2 illustrates the ternary diagram:
cyclohexane (solvent a, apolar)/glycerine (solvent b (polar))/bioactive substance: Bardac®.

Figure 3:
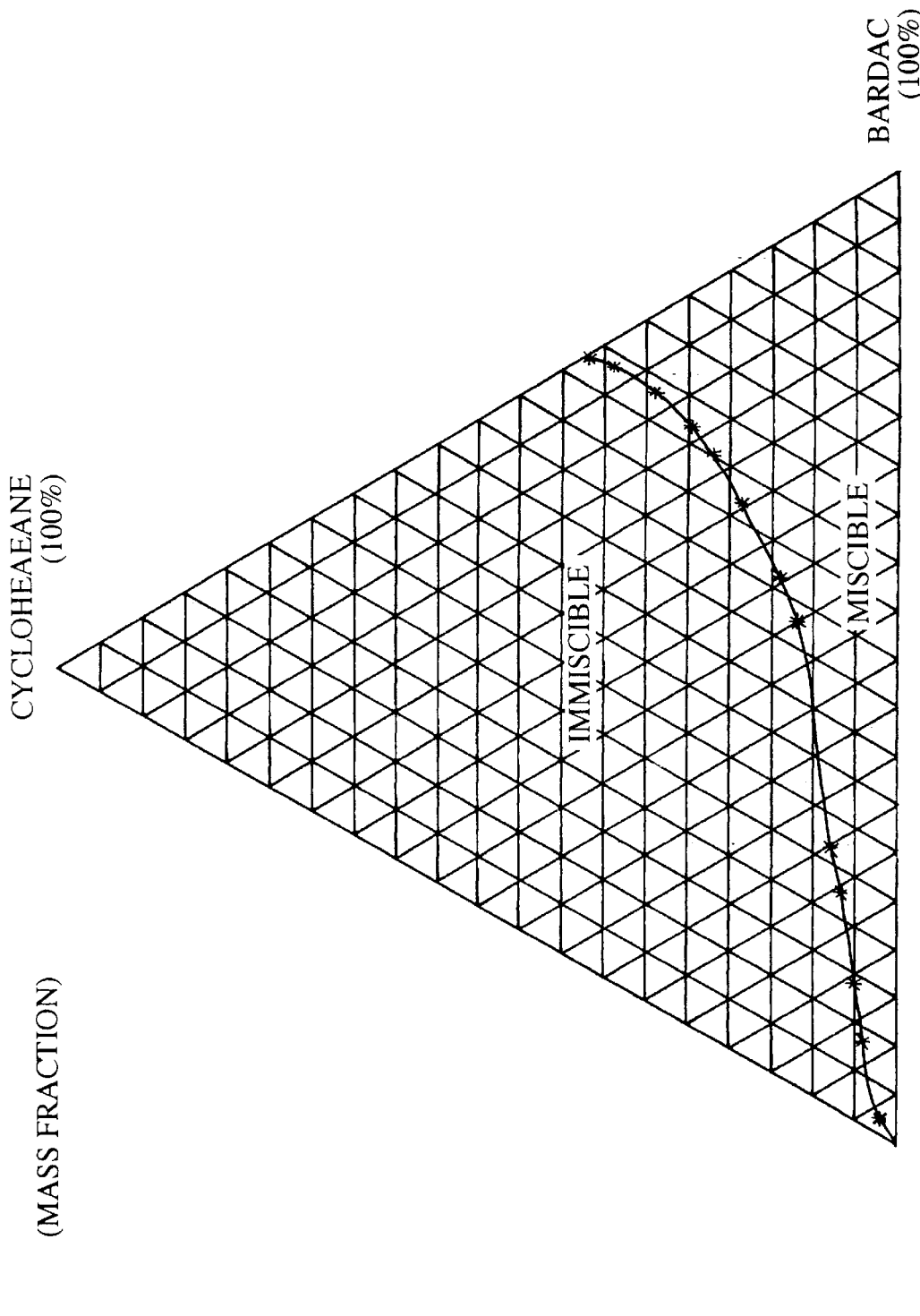

FIG. 3 illustrates the ternary diagram:
cyclohexane/PEG400/Bardac®.

Figure 4:
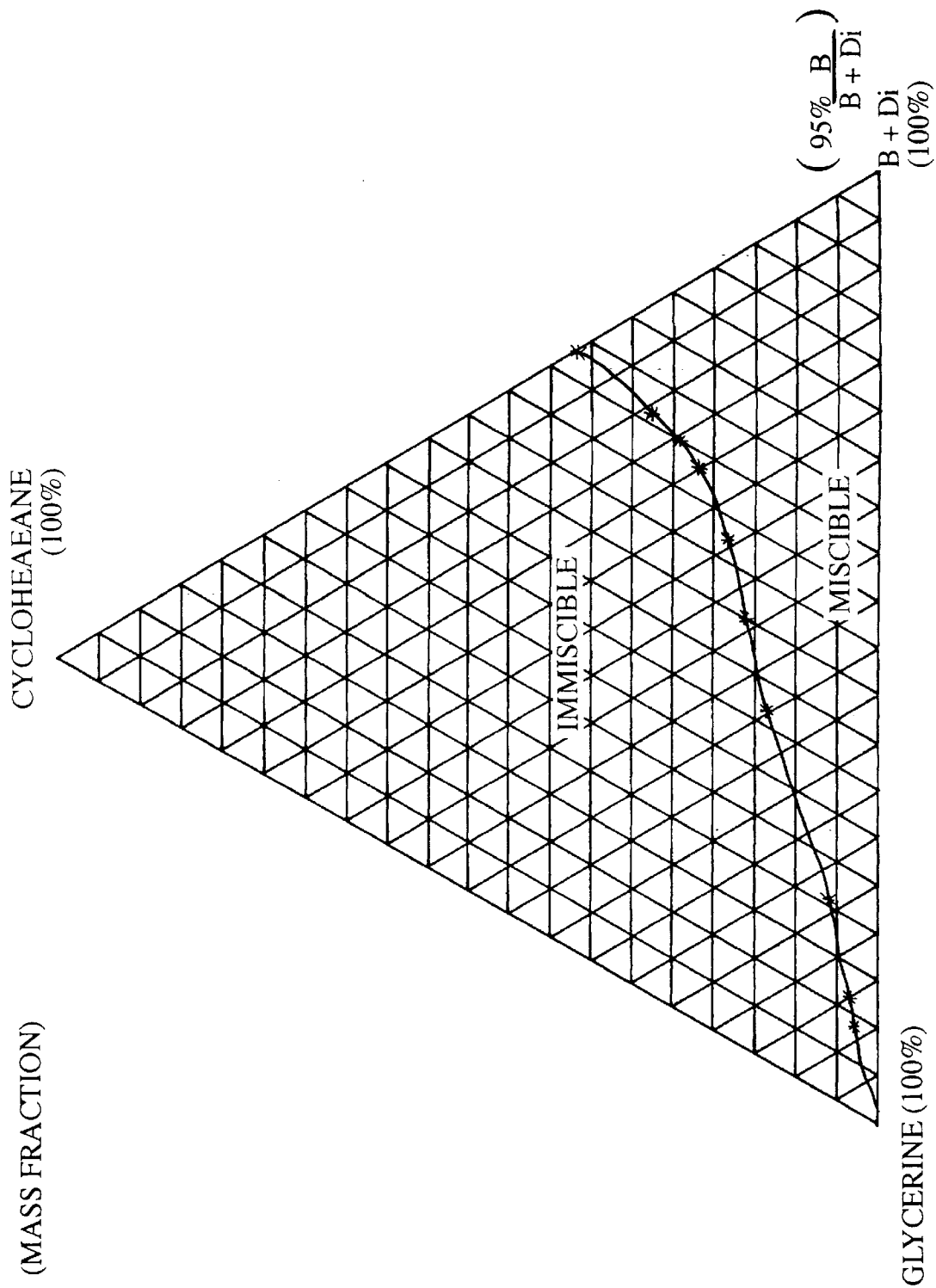

FIG. 4 illustrates the ternary diagram:
cyclohexane/glycerine/Bardac®+chlorhexidine digluconate (with 95% of Bardac®).

Figure 5:
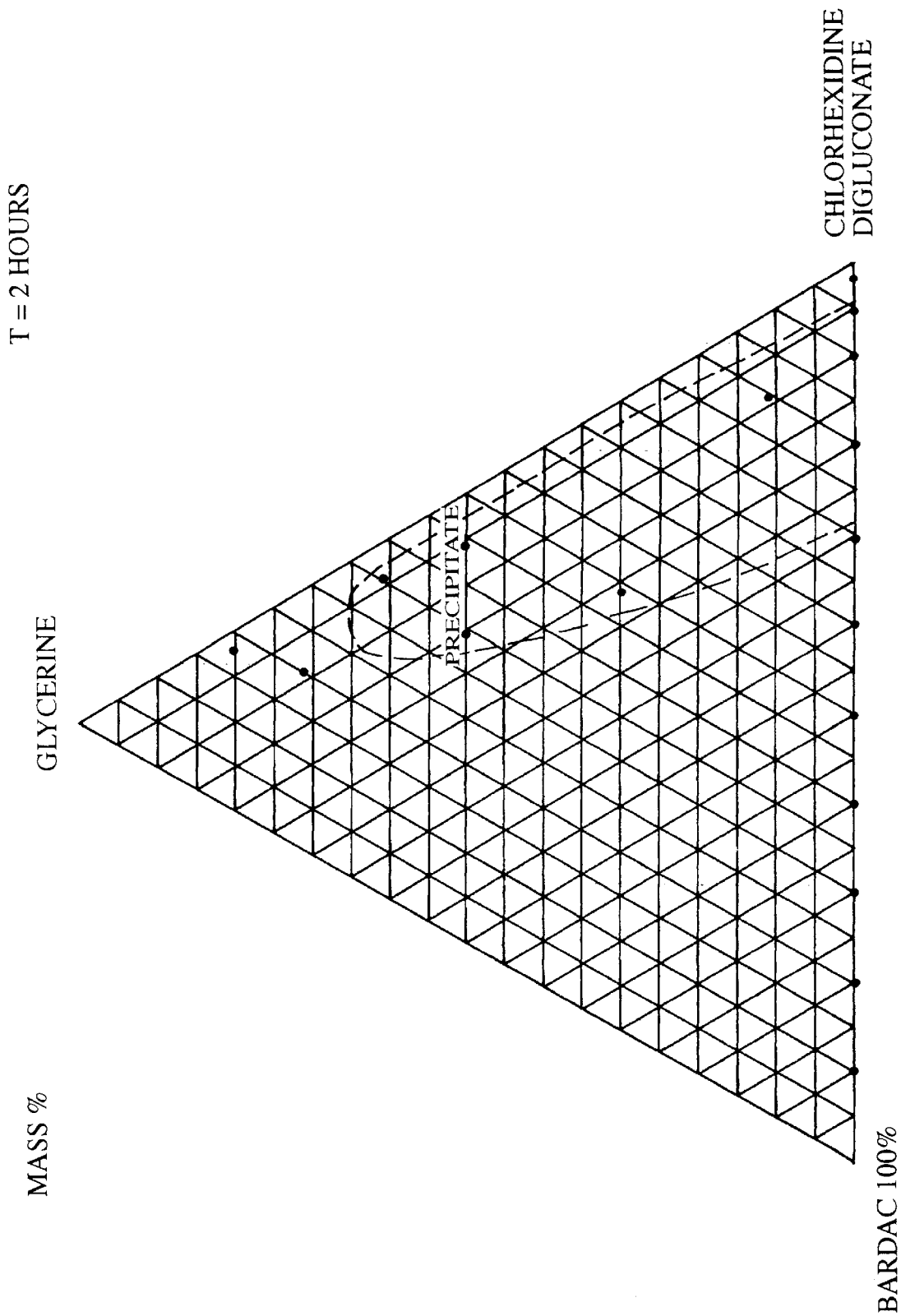

FIG. 5 illustrates the ternary diagram:
glycerine/Bardac®/chlorhexidine digluconate.

In general, the starting emulsion has one of the compositions according to the Table below:

| Continuous phase A (SEBS or PI + solvent a) | Disperse phase (biocides + solvent b) | Copolymer |
| --- | --- | --- |
| 5% to 20% in a cyclohexane + xylene mixture for example: - solvent a including cyclohexane (506 parts by weight) and xylene (131 parts by weight) - SEBS or PI elastomer (100 parts by weight) | 30 to 70 % of the quantity of elastomer (SEBS or PI) | 1.5 to 20%/ continuous phase A |

The composition of the disperse phase varies from 10 parts of biocides+90 parts of solvent b (PEG or glycerol) to 50 parts of biocides+50 parts of solvent b (PEG) with, for example, where the biocides are concerned:

90% of Bardac® 2270 E containing 70% of active principle,+10% of chlorhexidine digluconate or 80% of Bardac® 2270 E containing 70% of active principle,+20% of chlorhexidine digluconate or 75% of Bardac® as defined above,+25% of chlorhexidine digluconate, while conforming to the ternary diagram according to FIG. 5.

EXAMPLE 6

Preparation of gloves, fingerstalls or protective sheaths coated with an elastomer film in accordance with the invention.

The elastomer film in accordance with the invention is added, as coating of elastomer material, onto a layer of elastomer material previously converted into the desired shape by the usual manufacturing techniques, as follows:

A layer of elastomer in accordance with Application EP 306 389 is deposited onto a male mould made of ceramic, glass or similar material, defining the glove, the fingerstall or the sheath to be manufactured.

The mould coated with the said first layer is then subjected to a first pre vulcanization treatment and then, after immersion in a stabilized emulsion in accordance with the invention, the whole is vulcanized and is then removed from the mould.

As follows from the above, the invention is not limited in any way to those of its embodiments of use, of implementation and of application which have just been described more explicitly; on the contrary, it encompasses all the alternative forms thereof which can occur to the specialist in the subject, without departing from the context or from the scope of the present invention.

We claim:

1. Elastomer film comprising an active chemical substance in liquid form, said film comprising:

a dispersion of droplets consisting of a solution or dispersion of an active chemical substance in a polyol; and a stabilizing copolymer of said dispersion of droplets selected from the group consisting of
diblock of polyA-block-polyB copolymers,
triblock copolymers selected from the group consisting of polyB-block-polyA-block-polyB (BAB), polyA-block-polyB-block-polyA (ABA), polyA-block-polyB-block-polyC (ABC), and polyA-block-polyC-block-polyB (ACB) copolymers, and
graft copolymers selected from the group consisting of polyA-graft-polyB, polyB-graft-polyA, polyA-graft-(polyB and polyC), polyC-graft-(polyA and polyB) copolymers,
wherein said polyA blocks are immiscible with said droplets and are selected from the group consisting of polydienes, polyolefins, polyethers and silicones, wherein said polyB blocks are miscible with said droplets and are selected from the group consisting of polyoxyethylene, polyvinylpyrrolidone, polyacrylic acids, poly(vinyl alcohol) and quaternized poly(vinylpyridine), and wherein said polyC blocks are either miscible or immiscible with said droplets.

2. Elastomer film according to claim 1, wherein the proportions of polyA blocks are between 10 and 90 weight % and the proportions of polyB blocks are between 90 and 10 weight %, relative to the sum of the polyA and polyB blocks, and the proportions of polyC blocks are between 0% and 50 weight % relative to the total of blocks.

3. Elastomer film according to claim 1, wherein the number average molecular mass of the polyA and polyB blocks is between 1,000 and 500,000 daltons.

4. Elastomer film according to claim 1, wherein the polyA blocks are selected from the group consisting of polyisoprene, polybutadiene, polyisobutene, hydrogenated polybutadiene or hydrogenated polyisoprene, polystyrene, poly-tert-butylstyrene, polyoxypropylene and polydimethylsiloxane, which are miscible with a solution of elastomer in an apolar or weakly polar solvent a and not miscible with the polyol.

5. Elastomer film according to claim 1, wherein said film is selected from the group consisting of polybutadiene, polyisoprene, polychloroprene, SBR (styrene butadiene rubber), NBR (nitrile butadiene rubber), SBS (styrene butadiene styrene) or SIS (styrene isoprene styrene) or SEBS copolymers of a number average molecular mass which is higher than 50,000.

6. Elastomer film according to claim 1, wherein said active chemical substance is selected from the group consisting of anticorrosive agents and lubricants which are soluble in the polyol.

7. A glove, having a coating thereon, said coating comprising an elastomer film according to claim 1.

8. A fingerstall, having a coating thereon, said coating comprising an elastomer film according to claim 1.

9. A protective sheath, having a coating thereon, said coating comprising an elastomer film according to claim 1.

10. A rubbing seal, having a coating thereon, said coating comprising an elastomer film according to claim 1.

11. A dressing, having a coating thereon, said coating comprising an elastomer film according to claim 1.

12. A support having a coating thereon, said coating comprising an elastomer film according to claim 1.

13. Elastomer film according to claim 1, wherein the polyol is selected from the group consisting of polypropylene glycol, polyethylene glycol, glycerol, and mixtures thereof.

14. Elastomer film according to claim 1, wherein the active chemical substance is a biocide.

15. Elastomer film according to claim 14, wherein said biocide is selected from the group consisting of quaternary ammoniums, block copolymers with biocidal activity, biguanides, phthalaldehyde, phenolic compounds with biocidal activity, nonionic surfactants containing a polyoxyethylene block or hexamidine, and mixtures thereof.

16. Elastomer film according to claim 15 wherein said biocide is dimethyldidecylammonium.

17. Elastomer film according to claim 15 wherein said biocide is a polydimethylsiloxane-polyoxyethylene block copolymer.

18. Process for the preparation of an elastomer film, comprising:
(a) preparing an emulsion which comprises:
preparing a phase A by dissolving an elastomer in an organic solvent a;
preparing a phase B, by mixing at least one active chemical substance into an organic solvent b consisting of a polyol which is not miscible with the phase A;
adding to the phase A or to the phase B, in proportions of 0.1 to 50 weight %, a stabilizing block or graft copolymer selected from the group consisting of:
diblock of polyA-block-polyB copolymers,
triblock copolymers selected from the group consisting of polyB-block-polyA-block-polyB (BAB), polyA-block-polyB-block-polyA (ABA), polyA-block-polyB-block-polyC (ABC), and polyA-block-polyC-block-polyB (ACB) copolymers, and
graft copolymers selected from the group consisting of polyA-graft-polyB, polyB-graft-polyA, polyA-graft-(polyB and polyC), polyC-graft-(polyA and polyB) copolymers
wherein said polyA blocks are miscible with the phase A and are selected from the group consisting of polydienes, polyolefins, polyethers and silicones, said polyB blocks are miscible with the phase B and are selected from the group consisting of polyoxyethylene, polyvinylpyrrolidone, polyacrylic acids, poly(vinyl alcohol) and quaternized poly(vinylpyridine), and said polyC blocks are either miscible with solvent a or solvent b, or immiscible with solvents a and b;
dispersing the phase B in the phase A in order to obtain an emulsion in which the phase A forms the continuous phase and the phase B the disperse phase; and
(b) evaporating the organic solvent a, in order to obtain an elastomer film containing, in the form of a stable dispersion, droplets of solvent b and the active chemical substance.

19. Process according to claim 18, wherein the apolar or weakly polar organic solvent a is selected from the group consisting of aromatic, aliphatic and alicyclic hydrocarbons, and mixtures thereof.

20. Process according to claim 18 wherein the solvent b is selected from the group consisting of polypropylene glycol, polyethylene glycol, glycerol and mixtures thereof.

21. Process according to claim 18, wherein the proportions of polyA blocks are between 10 and 90 weight % and the proportions of polyB blocks are between 90 and 10 weight %, relative to the sum of polyA and polyB blocks, and the proportions of polyC blocks are between 0% and 50 weight % relative to the total of blocks.

22. Process according to claim 18, wherein the number average molecular masses of the polyA and polyB blocks are between 1,000 and 500,000 daltons.

23. Process according to claim 18, wherein the addition of a block or graft copolymer to a phase selected from the group consisting of phase A and phase B is in proportions of 0.1 to 25 weight %.

24. Process according to claim 19, wherein the apolar or weakly polar organic solvent a is selected from the group consisting of paraffinic hydrocarbons, cyclohexane, benzene, toluene, xylene, tetralin, decalin, and mixtures thereof.

25. Emulsion useful for the preparation of an elastomer film, comprising:
a phase A comprising an elastomer dissolved in an organic solvent a selected from the group consisting of apolar and weakly polar solvents,
a phase B dispersed in the phase A comprising at least one active chemical substance in solution or dispersed in a solvent b consisting of a polyol which is not miscible with the phase A, and
a block or graft copolymer selected from the group consisting of:
diblock of polyA-block-polyB copolymers,
triblock copolymers selected from the group consisting of polyB-block-polyA-block-polyB (BAB), polyA-block-polyB-block-polyA (ABA), polyA-block-polyB-block-polyC (ABC), and polyA-block-polyC-block-polyB (ACB) copolymers, and
graft copolymers selected from the group consisting of polyA-graft-polyB, polyB-graft-polyA, polyA-graft-(polyB and polyC), polyC-graft-(polyA and polyB) copolymers
wherein said polyA blocks are miscible with the phase A and are selected from the group consisting of polydienes, polyolefins, polyethers and silicones, said polyB blocks are miscible with the phase B and are selected from the group consisting of polyoxyethylene, polyvinylpyrrolidone, polyacrylic acids, poly(vinyl alcohol) and quaternized poly(vinylpyridine), and said polyC blocks are either miscible with solvent a or solvent b or immiscible with solvents a and b.

26. Process for the preparation of stable emulsions comprising:
preparing a phase A by dissolving the elastomer in an organic solvent a;
preparing a phase B by mixing at least one active chemical substance into an organic solvent b which is not miscible with the phase A;
adding to the phase A or to the phase B, in proportions of 0.1 to 50 weight %, a block or graft copolymer comprising at least polyA blocks which are miscible with the phase A and polyB blocks which are miscible with the phase selected from the group consisting of:
diblock of polyA-block-polyB copolymers,
triblock copolymers selected from the group consisting of polyB-block-polyA-block-polyB (BAB), polyA-block-polyB-block-polyA (ABA), polyA-block-polyB-block-polyC (ABC), and polyA-block-polyC-block-polyB (ACB) copolymers, and
graft copolymers selected from the group consisting of polyA-graft-polyB, polyB-graft-polyA, polyA-graft-(polyB and polyC), polyC-graft-(polyA and polyB) copolymers
wherein said polyA blocks are miscible with the phase A and are selected from the group consisting of polydienes, polyolefins, polyethers and silicones, said polyB blocks are miscible with the phase B and are selected from the group consisting of polyoxyethylene, polyvinylpyrrolidone, polyacrylic acids, poly(vinyl alcohol) and quaternized poly(vinylpyridine), and said polyC blocks are either miscible with solvent a or solvent b, or immiscible with solvents a and b; and
dispersing the phase B in the phase A in order to obtain an emulsion in which the phase A forms the continuous phase and the phase B the disperse phase.

27. Process according to claim 26, wherein the addition of a block or graft copolymer to a phase selected from the group consisting of phase A and phase B is in proportions of 0.1 to 25 weight %.

* * * * *

UNITED STATES PATENT AND TRADEMARK OFFICE
CERTIFICATE OF CORRECTION

PATENT NO. : 5,804,628
DATED : September 8, 1998
INVENTOR(S) : Busnel et al.

It is certified that error appears in the above-identified patent and that said Letters Patent is hereby corrected as shown below:

Column 11, line 12, after "phase" insert -- B] --.

Signed and Sealed this

Twenty-sixth Day of January, 1999

Attest:

Attesting Officer

Acting Commissioner of Patents and Trademarks